United States Patent [19]

Proelss

[11] 4,347,313

[45] Aug. 31, 1982

[54] ANALYTICAL DETERMINATION OF LIPASE

[75] Inventor: Henning F. Proelss, Birmingham, Ala.

[73] Assignee: Boehringer Mannheim GmbH, Mannheim, Fed. Rep. of Germany

[21] Appl. No.: 210,120

[22] Filed: Nov. 24, 1980

Related U.S. Application Data

[63] Continuation of Ser. No. 881,756, Feb. 27, 1978, abandoned.

[51] Int. Cl.$^3$ .......................... C12Q 1/26; C12Q 1/44
[52] U.S. Cl. ......................................... 435/19; 435/25
[58] Field of Search ................................. 435/19, 25

[56] References Cited

U.S. PATENT DOCUMENTS

| Re. 29,498 | 12/1977 | Meiattini | 435/25 |
| 3,689,364 | 9/1972 | Härtel et al. | 435/19 |
| 3,838,011 | 9/1974 | Hagen et al. | 435/10 |
| 3,917,515 | 11/1975 | Goldberg | 435/19 |

OTHER PUBLICATIONS

Whitaker, *Principles of Enzymology for the Food Sciences*, Marcel Dekker, Inc., New York, 1972, pp. 609, 610, 615.
Proelss et al., Clin. Chem., 23(3), 522–531 (1977).

*Primary Examiner*—Esther M. Kepplinger
*Attorney, Agent, or Firm*—Felfe & Lynch

[57] ABSTRACT

A test for lipase activity is provided wherein trilinolein, or an equivalent as defined herein, is employed in an emulsified form as a substrate. Reduced incubation times and improved accuracy are obtained by providing an excess of lipoxygenase to convert the linoleic acid product of lipolysis to linoleic acid hydroperoxide which is measurable with great accuracy at low concentrations by spectrophotometric or kinetic assay techniques, for example.

21 Claims, No Drawings

ANALYTICAL DETERMINATION OF LIPASE

This is a continuation, of application Ser. No. 881,756, filed Feb. 27, 1978, now abandoned.

BACKGROUND OF THE INVENTION

The usefulness of the determination of lipase activity in physiological fluids, including serum and duodenal fluid, for example, in early diagnosis of pancreatic diseases and monitoring the clinical course thereof has been generally acknowledge in the past. However, technical difficulties as well as problems with specificity and sensitivity of existing lipase methods have generally hindered the more widespread use of this enzyme as a primary laboratory indicator of pancreatic function.

The most widely accepted methods for measuring lipase activity in biological fluids usually employ olive oil as a substrate and rely on titration, with standardized sodium hydroxide of the fatty acids liberated during a 24 hour incubation period. Some major disadvantages of these types of methods include long incubation times, resulting in nonlinearity and reduced specificity; large sample requirements; the requirement for highly concentrated and stable olive oil emulsions, which are difficult and cumbersome to prepare; and the difficulties of reproducing the end point in the titration of the extremely weak long-chain fatty acids. Colorimetry of the free fatty acids produced by lipolysis of an olive oil substrate (in the form of their copper soaps, after extraction into a lipid solvent) permits shorter incubation times (10-30 minutes), but involves many tedious manipulations which limits its usefulness in a routine laboratory. The procedures described above, including variations thereof employing sensitive fluorescent pH indicators, for example, in addition to the described difficulties, lack the desired sensitivity and precision in the normal range of lipase activities.

In addition to the above described methods, turbidimetric methods of lipase analysis have been employed in the past, but the substrate concentrations used are suboptimal to permit the rate of substrate clearance to be measured in a reasonably accurate photometric range and initial increases in absorbance and nonlinear absorbance changes throughout the entire reaction period have been reported for patients' samples, indicating problems with some of these procedures. In addition to the olive oil substrate, several synthetic soluble chromogenic and fluorogenic substrates, mostly monoesters of long-chain fatty acids, have been proposed for use in the measurement of lipase activity in serum. However, it has been conclusively proved that pancreatic lipase does not act on soluble esters but is active only when adsorbed at an oil/water interface. Thus, the nonemulsified state of these types of substrates indicates limited usefulness as analytical tools for measuring pancreatic lipase activity. Lipase activity has also been determined by radial enzyme diffusion, based on measurement of the cross-sectional area of the clearing of an olive oil emulsion suspended in buffered agarose gel. The disadvantages of this method are that two hour incubation times are required, accurately measuring small diameters of the clear zone is difficult, and it is necessary to calibrate with secondary standards.

Thus, a method for the determination of lipase activity in biological fluids which has reduced incubation time, can employ relatively small amounts of sample fluids, and which is highly specific and sensitive is desirable. Further, a lipase activity measurement procedure which can be performed simply, using readily available laboratory equipment, would be advantageous.

SUMMARY OF THE INVENTION

The method of the present invention overcomes the disadvantages of the lipase activity tests briefly described above by employing a coupled enzymatic reaction sequence to convert the primary product of lipolysis into a chemical compound that may be measured with greater speed and ease and with greater sensitivity, precision, and accuracy than is possible in the analysis of free long-chain fatty acids by either titrimetric or indirect photometric methods following solvent extraction. Basically, the method comprises adding a sample of biological fluid to a substrate emulsion to thereby induce lipolysis. The substrate employed is preferably trilinolein but can be an equivalent thereof as further defined hereinbelow. Either at the same time or shortly thereafter, an amount of lipoxygenase is added which is effective to convert the linoleic acid produced by lipolysis to linoleic acid hydroperoxide, the conversion being effected at a rate substantially greater than that at which the linoleic acid is produced. The hydroperoxide can then be measured by colorimetry, uv-spectrophotometry, or kinetic assay techniques. A lipoxygenic endpoint assay requires only about 15 minutes and the kinetic version of the tests (usually employing an oxygen electrode) only a few minutes for completion which makes the assay well suited for an emergency procedure. Further, increased sensitivity is achieved by the coupled enzymatic reaction as compared to the standard lipase methods that measure the weak long-chain fatty acids produced during incubation of the sample with olive oil (or triolein) emulsions by titration with alkali, thus permitting the use of microsamples which makes the procedure ideally applicable to pediatric applications.

DETAILED DESCRIPTION OF THE INVENTION

The rapid enzymatic micromethod for specific determination of the diagnostically important enzyme lipase (glycerol ester hydrolase, E.C. No. 3.1.1.3) of the present invention employs a coupled enzymatic reaction sequence whereby the free linoleic acid produced by lipolysis of an emulsified trilinolein substrate (or a substrate formulation employing one of the other triglycerides set forth in detail below) is converted to more easily identifiable linoleic acid hydroperoxide. The conversion is accomplished by providing an excess amount of lipoxygenase (also known as lipoxidase linoleate:oxygen oxidoreductase E.C. 1.99.2.1) so that the rate of formation of the linoleic acid from lipolysis is the rate limiting step of the coupled enzymatic reaction. The basic coupled enzymatic reaction sequence can be schematically depicted in the following manner:

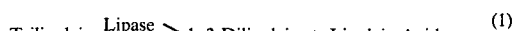

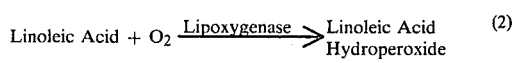

Because an excess amount of lipoxygenase is employed, the rate of formation of linoleic acid, which is directly proportional to the activity of lipase under the employed conditions of substrate saturation, may be measured by the rate of production of linoleic acid hydroperoxide, or the rate of consumption of oxygen. Suitable reaction conditions for the coupled enzymatic reaction sequence are 30° C. at a pH of 8.8. Under these conditions, the incubation time for the coupled enzyme reaction is about 10 minutes and the reaction can be stopped by the addition of alcohol. Thus, when lipoxygenic endpoint assay techniques are employed, the entire procedure takes only about 15 minutes, and when kinetic assay techniques are employed the actual measurement of lipase activity takes place during the incubation period. In comparison, the standard titrimetric olive oil procedures typically require from 3 to 24 hours of incubation to generate adequate amounts of titratable acid and the continuous sampling version of these types of methods requires a pH-stat instrument which is generally unavailable to most clinical laboratories. The coupled enzyme reaction sequence set forth above is also superior to the presently available methods for measuring lipase activity by using soluble substrates in that trilinolein (and its equivalents described hereinbelow) are not hydrolized by the various carboxylesterases and therefore does not yield false positive results in cases where these non-specific esterases are e coupled enzymatic reaction also provides for a drastic increase in sensitivity when compared to standard lipase methods that measure the weak long-chain fatty acids produced during incubation of the sample with olive oil emulsions by titration with alkali. This increase in sensitivity permits the use of microsamples, which makes the test well suited for pediatric patients.

A further advantage of the lipase method of the present invention is that preparation of the substrate emulsion can be performed rapidly and in a technically simple and non-critical manner since adequate oil/water interface is easily obtained when microsamples are employed. This should be contrasted with the preparation of olive oil emulsions for the existing standard titrimetric methods which preparation is a technically involved cumbersome procedure requiring the addition of gum acacia (or a similar emulsifier) in order to obtain a stable emulsion of high oil/water interfacial area, which is crucial for the success of the method.

While the naturally occuring glycerol ester trilinolein is the preferred substrate material, it will be apparent to one skilled in the art that other natural or synthetic, simple or mixed triglycerides (triacylglycerols) can be employed. Basically, the requirements of other useful natural or synthetic, simple or mixed triglycerides are that the component fatty acids, esterified to glycerol in 1,3-(or −) position meet the structural requirements for a good substrate for the enzyme lipoxygenase, i.e. result in high rates of formation of hydroperoxide in the presence of oxygen. Present knowledge of the enzyme suggests that a methylene interrupted cis-diene system with double bonds extending from carbon atom #6 to 7 ($\omega 6$) and from carbon atom #9 to 10 ($\omega 9$) counting from the methyl end of the fatty acid must be present according to:

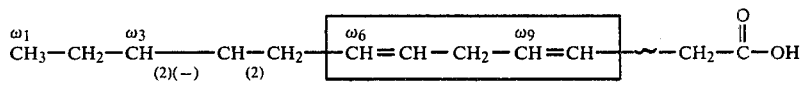

Other doublebonds (e.g. $\omega 3$, $\omega 12$, $\omega 15$-) may or may not be present.

The general structure for a qualifying triglyceride may be depicted schematically as follows:

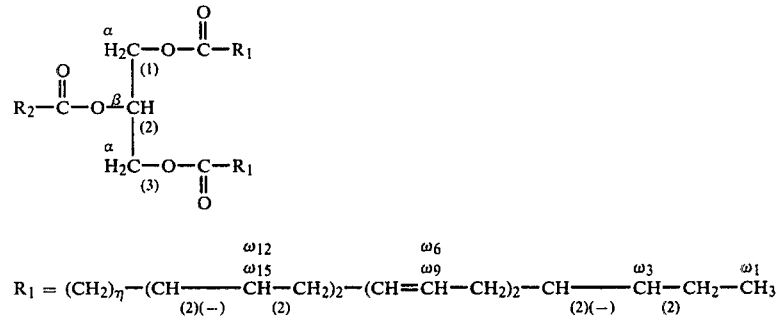

$\eta = 1$, 3 or 5 for naturally occurring and 1, 2, 3, 4 or 5 for synthetic fatty acids.

$R_2 = R_1$ for the preferred simple triglyceride substrates.

$R_2$ may be any saturated or (poly)unsaturated fatty acid alkyl chain in case of mixed triglyceride substrates. This is so because the 2 (or $\beta$) esterlinkage is not attacked by lipase during the initial reaction phase, and consequently, there are no specific structural requirements for the fatty acid bound in this position.

Trilinolein (or an equivalent triglyceride of the above specified structural formula) can be prepared in emulsified form relatively easily for use as a substrate with which lipase will conjugate according to the coupled enzymatic reaction sequence of the present invention. For example, trilinolein, which is available in 100 mg/ampules, can be dissolved in an ethanol/acetone solvent and stored at 0°-4° C. to form a substrate stock solution which can be emulsified by blending with a working buffer which provides the proper pH for the enzymatic reactions. A suitable working buffer can be prepared from sodium deoxycholate dissolved in tris(hydroxymethyl)aminomethane (hereinafter sometimes referred to as Tris) with sufficient hydrochloric acid to adjust the pH to the desired level. Alternatively, barbital buffer may be substituted for Tris. Substrate emulsions can be prepared by mixing the working buffer with the substrate stock solution and blending, at maximum speed, in a commercial blender for about 5 minutes. Preferably the substrate emulsions are prepared freshly each day.

Lipoxygenase (linoleate:oxygen oxidoreductase, EC 1.99.2.1) necessary to perform the specific conversion of the linoleic acid produced by lipolysis to linoleic acid hydroperoxide, can be prepared, in stock solution form, by admixing lyophilized lipoxygenase of sufficient activity with the appropriate volume of working buffer (described above with relation to the substrate emulsion) to obtain the stock solution having an activity of $1.40 \times 10^6$ S.U.*/ml ($\simeq$168,000 I.U./ml at 25° C.). This lipoxygenase stock solution should be stored at temperatures at from about 0° to about 4° C. A lipoxygenase working solution having an activity of about 140,000 S.U./ml ($\simeq$16,800 I.U./ml at 25° C.) can then be prepared by diluting the lipoxygenase stock solution 1:10 with more working buffer and should be prepared freshly each day. The coupled enzyme reaction sequence of the present invention is made possible by the high specificity of lipoxygenase for free linoleic acid and the similarity of the pH optima of both enzymes (pH 8.8 for lipase, pH 8.3 for lipoxygenase). The lipoxygenase employed in the present invention can be isolated from soybean-flour extracts.

*Definition of spectrophotometric unit (S.U.): One (1) S.U. will cause an increase in absorbance at 234 nm ($\Delta A_{234}$) of 0.001 at 25° C. when linoleic acid is the substrate in 3 ml volume at pH 9.0 (1 cm light path). 1 S.U. is equivalent to the oxidation of $0.12\mu$ mole of linoleic acid, i.e. 0.12 International Units (I.U.B. units or I.U.) at 25° C.

While any biological fluid suspected of containing the enzyme lipase may be employed with the substrate emulsion, and lipoxygenase working solution set forth above to perform the coupled enzymatic reaction sequence of the present invention, the biological fluids of greatest interest are blood serum and duodenal fluid. Because of the extreme sensitivity of the test procedure of the subject invention, microsamples of blood serum and duodenal aspirate can be employed. For example, 10 $\mu$l of serum sample (20 $\mu$l with test blank) can be employed in most cases. A like amount of diluted duodenal aspirate can be employed.

Thus, the above described reagents, that is substrate emulsion, lipoxygenase working solution and biological sample fluid are all the reagents necessary to form the coupled enzymatic reaction sequence of the present invention. Of course, other reagents will be useful depending upon the analytical method employed to determine lipase activity. However, for example, when kinetic assay techniques are employed which measure directly the rate of oxygen consumption by the reaction between linoleic acid and oxygen (see equation 2 above) no other reagents need be employed.

The kinetic variables which influence the coupled enzymatic reaction of the subject invention, including substrate concentration, effects of sample matrix, effect of blending times and speeds on the substrates, effect of bile salts, effects of pH, effect of temperature, effect of lipoxygenase activity and effect of concentration of oxygen in the system were studied in order to better understand the operating parameters of the system. The results of these studies will aid one skilled in the art in the practice of the subject invention.

With regard to substrate concentration, it should be noted that since the lipase acts on the oil/water interface only, the interfacial area of the substrate/buffer emulsion takes the place of the substrate concentration in the kinetic equation for homogeneous systems. However, if the substrate is insoluble in water, and the degree of emulsification is identical for all substrate concentrations used, the interfacial area increases linearly with increasing substrate concentration. Because of the technical difficulties of measuring accurately the interfacial area of emulsions, the conditions of emulsification were kept constant throughout the study and the reaction rates were expressed as a function of the trilinolein concentrations. Basically, with respect to trilinolein, it was determined that at substrate concentrations of less than about $1.0 \times 10^{-4}$ mol/liter there is insufficient substrate for saturation of the enzyme and at substrate concentrations above approximately $4 \times 10^{-4}$ mol/liter there is an apparent decrease in the maximum velocity of the substrate-lipase reaction, indicating some form of substrate inhibition.

The effect of the sample matrix was studied by comparing serial dilutions of pancreatitis serum with heat-deactivated human serum and solutions of 10 grams of bovine serum albumin in 1 liter of working buffer. The differences in the sample matrix were not significant for lipase activities up to 1,000 U/liter. Apparently, at the high substrate concentration chosen for the assay, the velocity of the reaction is at a maximum whether the samples have been diluted or not and is equal for identical lipase activities, independent of the sample matrix.

The effect of blending times and speeds in preparation of the substrate emulsion was also investigated. Basically, it was found that substrates prepared simply by vortex-mixing trilinolein for 3 to 5 minutes with the substrate buffer led to data indicating inadequate interface area or instability of the emulsion, or both. It was determined that the best results were obtained with homogenized substrates, prepared by blending the chilled working buffer in a commercial blender at a maximum speed with trilinolein for 3 to 5 minutes. Blending for more than 5 minutes does not apparently further increase either the linear range or the stability of the substrate and may result in undesirable heating of the substrate. Substrates prepared by the methods suggested above are stable for three to four days, if kept refrigerated.

The effect of various concentrations of bile salts, and specifically deoxycholate on the overall reaction rate was studied. For both normal and pancreatitis serum samples maximum activity was observed at 3.6 mmol of deoxycholate per liter. Other bile salts (glycocholate, taurocholate) have a similar effect.

The effect of pH on the rate of trilinolein hydrolysis of both normal and pancreatitis serum was studied in the range of 7.6 to 9.4 at 30° C. A trilinolein substrate, prepared in 50 mmol/liter at 25° C., was divided into several aliquots, which were adjusted individually by dropwise addition of 12 mol/liter HCl to the desired pH values. The results of these tests indicate that lipase of normal serum loses its activity faster than that in diluted pancreatitis serum on either side of the pH optimum which is about 8.8 at 30° C. for both samples.

The effect of temperature on the rate of trilinolein hydrolysis was studied in the range between 20° and 40° C. The pH was maintained at exactly 8.8 at all reaction temperatures, by computing the corresponding pH at room temperature from the temperature coefficient of Tris buffer (0.025/°C.), and adjusting the substrate pH values at 25° C. accordingly by dropwise addition of 12 mol/liter HCl, or 10 mol/liter NaOH. The study shows that between 37° and 40° C. an actual decrease in activities is observed, indicating progressive heat denaturation of either lipase or lipoxygenase, or both. These studies indicate that 30° C. should be the recommended reaction temperature for the assay of the present invention.

In order to determine the degree of saturation of lipoxygenase, diluted pancreatitis serum was analyzed under the conditions of the assay of the present invention, using different lipoxygenase activities. At lipoxygenase activities of 1000 S.U./liter of substrate ($\simeq$120 I.U./liter at 25° C.), the lipase-catalyzed hydrolysis of trilinolein apparently becomes rate limiting. The actual lipoxygenase activity used in the final assay is about 1400 S.U./liter ($\simeq$168 I.U./liter) in order to compensate for partial loss of enzyme activity by potential serum inhibitors of this enzyme. Thus, lipoxygenase activities of at least 1,000 S.U./liter of substrate (120 I.U./liter at 25° C.) are necessary in order that the conversion of trilinolein to linoleic acid by lipase be the rate limiting reaction.

Finally, the effect of the concentration (partial pressure) of oxygen was studied. According to the second equation of the coupled enzymatic reaction sequence of the present invention, one mole of oxygen is consumed for each mole of linoleic acid converted to its hydroperoxide. In order to determine whether or not atmospheric conditions would provide sufficient oxygen to insure the reaction rate would remain unaffected, reactions using atmospheric conditions were compared to those carried out under a continuous stream of pure oxygen, using a preoxygenated buffer. No difference in either the velocity or the linearity of the reaction with respect to time and activity were noted for the latter type reactions, thus indicating that the test can be carried out with non-oxygenated buffer in open test tubes in normal laboratory atmosphere.

EXAMPLE PROCEDURES

In order to more fully illustrate the present invention, example procedures are set forth below wherein colorimetric, spectrophotometric, and kinetic assay techniques are employed in combination with the coupled enzymatic reaction sequence set forth above to determine lipase activity. It is not intended that the scope of the present invention be limited to those methods of analysis, and they are set forth as exemplary only.

The starting materials, and reagents prepared therefrom, are set forth below and are exemplary of those which can be employed. Modifications thereof will be apparent to one skilled in the art:

Sodium deoxycholate, AR.

Acid-alcohol solution, 2.62 g/liter. Dilute 6.0 ml of 12 mol/liter hydrochloric acid (AR) to 1 liter with absolute ethanol (AR).

Ferrous ammonium sulfate (AR), 0.13 mol/liter. Dissolve 250 mg in 5.0 ml of hydrochloric acid, 30 g/liter.

Ammonium thiocyanate (AR), 2.63 mol/liter. Dissolve 20 g in deionized water, dilute to 1 dl.

Lipoxygenase (linoleate:oxygen oxidoreductase, EC 1.99.2.1.), activity, 165,000 S.U./mg ($\simeq$19,800 I.U./mg at 25° C.)

Lipoxygenase stock solution, $1.40 \times 10^6$ S.U./ml. Dissolve 85 mg in 10.0 ml of working buffer. Store 0.1 ml aliquots at 0°–4° C.

Lipoxygenase working solution, 140,000 S.U./ml ($\simeq$16,800 I.U./ml at 25° C.). Dilute a 0.1 ml aliquot of stock solution with 0.9 ml of working buffer. Prepare freshly each day.

Trilinolein, 100 mg/ampule.

Trilinolein stock solution, 20 mg/ml. Dissolve the contents of a 100 mg ampule in 5.0 ml of ethanol/acetone (3/2 by vol.) Store at 0°–4° C.

Working buffer. Dissolve 1.5 g (3.6 mmol) of sodium deoxycholate in 1 liter of tris(hydroxymethyl)aminomethane (Tris), 50 mmol/liter. Adjust the pH to 8.9 at 25° C. by dropwise addition of hydrochloric acid, 12 mol/liter. Store at 2°–6° C.

Substrate emulsion, 0.34 mmol/liter. Transfer 50 ml of the working buffer to the blender vessel, add 0.75 ml of trilinolein stock solution, blend at maximum speed for 5 min. Prepare freshly each day.

Linoleic acid, 1 g/ampule.

Linoleic acid stock solution, 36 mmol/liter. Dissolve the contents of a 1 g ampule in 1 dl of absolute ethanol. Store at 0°–4° C.

Linoleic acid working standard, 50 $\mu$mol/liter. Dilute 0.14 ml of stock solution to 1 dl with working buffer.

Solutions for linoleic acid standard curve. Dilute 280 $\mu$l of stock solution to 1 dl with working buffer, 100 $\mu$mol/liter. Serially dilute this standard with working buffer to yield standards of 75, 50 and 25 $\mu$mol/liter.

Control sera.

Bovine Serum Albumin, 10 g/dl in deionized water.

COLORIMETRIC ENDPOINT ASSAY

The amount of linoleic acid hydroperoxide produced by the coupled enzymatic reaction sequence of the present invention within a 10 minute incubation period can be measured photometrically at 480 nm after dissolving the reaction mixture in acid alcohol, using the oxidation of ferrous to ferric ion by hydroperoxide and the detection of the ferric ion by thiocyancte according to the following equations:

$$R-OOH + 2Fe^{2+} + 2H^+ \rightarrow R-OH + 2Fe^{3+} + H_2O \quad (3)$$

$$Fe^{3+} + 3SCN^- \rightarrow [Fe(SCN)_3] \text{ (red complex)} \quad (4)$$

Lipase activity is computed in IUB units, with use of primary linoleic acid standards that are submitted to the same reaction sequence. The contribution of traces of free linoleic acid and of lipid peroxides, present in commerical batches of trilinolein, is subtracted in a substrate blank, the contribution of endogenous and exogenous sample constituents is compensated for in individual test blanks, and the contribution of the color reagents is subtracted using reagent blanks.

The following procedure can be employed to perform the colorimetric endpoint assay embodiment of the present invention.

(1) Label a series of test tubes, two for each patient's serum (T and TB) plus one each for a standard (S), "substrate blank" (SB), and "reagent blank" (RB).

(2) To the tubes labeled T and SB, add 1 ml of substrate emulsion. To the S tube add 1 ml of the 50 $\mu$mol/liter linoleic acid standard. To the tubes labeled TB and RB, add 1 ml of working buffer.

(3) Place all the tubes in a 30° C. waterbath for 5 minutes.

(4) In an exactly timed sequence (a 15 second interval is recommended), add 10 $\mu$l of serum, add 10 $\mu$l of lipoxygenase working solution, in that order, to the tubes labeled T and TB, vortex-mixing for 5 seconds after each addition, and replace it in the waterbath. To the tubes labeled S and SB add 10 $\mu$l of lipoxygenase only, and vortex-mix for 5 seconds replacing them in the waterbath.

(5) After exactly 10 minutes, and in the same timed interval, remove each tube from the waterbath and add 6 ml of acid/alcohol reagent from a dispenser and vortex-mix briefly. It should be noted that because the absorbance of the test blanks does not change measurably during the 10 minute incubation period, it is not necessary to adhere to a timed sequence for the test blanks, and the acid-alcohol reagent may be added to the TB tubes at any time while T tubes are still incubating.

(6) Add 20 µl of ferrous ammonium sulfate reagent to all tubes and vortex-mix briefly.

(7) Add 100 µl of ammonium thiocyanate reagent to all tubes and vortex-mix briefly.

(8) Measure the absorbance of each sample at 480 nm against the reagent blank (RB).

The enzymatic activity of the serum sample can be calculated using the following formula:

$$\text{Lipase activity } (U/\text{liter}) = \frac{\Delta A_T}{A_s} \times 500$$

where $$\Delta A_T = A_T - A_{TB} - A_{SB}$$

The above formula was derived from the following known factors:
sample dilution factor: 100 (10 µl→1 ml)
incubation time: 10 minutes
linoleic acid standard: 50 µmol/liter
50 µmol/liter substrate is equivalent to 5 mmol/liter sample
5 mmol/liter per 10 min is equivalent to 500 µmol/liter per min (500 U/liter)

Alternatively, the concentration of linoleic acid corresponding to $\Delta A_T$ can be read from the linoleic acid standard curve in mol/liter and multiplied by 10 to obtain the lipase activity in U/liter.

UV-SPECTROPHOTOMETRIC ENDPOINT ASSAY

The linoleic acid hydroperoxide concentration can be measured directly in an ethanol diluted reaction mixture via its UV absorption at 234 nm ($E_{234} \simeq 23,000$ at 37° C.) using a narrow-band UV-Spectrophotometer. This procedure is recommended especially for the assay of lipase activity in duodenal aspirates.

Duodenal aspirates can be prepared for use as samples in the method of the present invention by centrifuging specimens obtained by intubation at 0°–8° C. at 4,000 g for approximately 10 minutes to remove suspended particles. The duodenal aspirate is then diluted 40–80 fold with a 10 g/liter solution of bovine serum albumin.

Next, the procedure set forth in steps (1) through (5) above with respect to the colorimetric assay procedure, are repeated substituting the diluted duodenal juice for the serum sample.

After the above steps and procedures have been performed, the absorbence of each sample is read in 1 cm quartz cuvets at 234 nm against the reagent blank. Lipase activity in the unknown sample can then be calculated using the same equation set forth above with respect to the colorimetric assay technique.

Alternatively, the concentration of linoleic acid hydroperoxide ($C_{LAH}$) corresponding to $\Delta A_T$ may be determined directly (without use of standards) once the molar extinction coefficient of linoleic acid hydroperoxide at 234 nm ($E_{234}$) has been measured with the spectrophotometer employed. This calculation can be performed using the following equations:

$$C_{LAH}\left[\frac{\mu\text{mol}}{\text{liter}}\right] = \frac{\Delta A_T \times 10^6}{E_{234}*}$$

Lipase activity $(U/\text{liter}) = C_{LAH} \times 10**$

*$E_{234}$ (37° C.) $\simeq$ 23,000
**$\frac{\text{Dilution factor of sample}}{\text{Incubation time (min)}} = \frac{100}{10} = 10$

KINETIC ASSAY USING A PO₂ ELECTRODE

Using this method of analysis the reaction is monitored by the decrease in oxygentension ($pO_2$) as linoleic acid produced during lipolysis reacts with an equimolar amount of dissolved oxygen to form linoleic acid hydroperoxide, using a $pO_2$ electrode. Lipase activity is computed with the initial rate of decrease of $pO_2$ in the reaction mixture after addition of sample lipoxygenase to the trilinolein emulsion substrate. The apparatus necessary to perform this type of analysis includes micro $pO_2$ electrodes suitable for blood gas analysis with associated signal amplifier and read-out device (strip-chart recorder, printer, etc.). A thermostat controlled reaction chamber (30° C.), containing the sensing element of the oxygenelectrode and a magnetic stirrer. The assay is carried out in the following manner:

(1) 1 ml of the previously aerated substrate emulsion is pipetted into the reaction chamber. The electrode is allowed to stabilize. The recorder is set to maximum reading.

(2) 10 µl of sample (serum, duodenal aspirate, control, etc.) and 10 µl of lipoxygenase working solution are added with a micro-pipet. The magnetic stirrer is activated for 5–10 seconds.

(3) The decrease in oxygen tension is recorded as the reaction proceeds for approximately 3–6 minutes.

(4) The slope of the $pO_2$/time curve is measured as soon as it becomes linear.

(5) The system is zero-rated by repeating steps 1–4 as described, but omitting the sample addition of step 2.

(6) The rate obtained using the substrate blank (SB) is subtracted from the rate obtained with the test sample (T) to obtain the net oxygen consumption rate ($\Delta r_T = r_T - r_{SB}$).

(7) A suitable lipase reference standard is then assayed the same way as the unknown sample and its net oxygen consumption rate is calculated ($\Delta r_{ref}$). The lipase activity in the unknown test sample can be computed as follows:

$$\text{Lipase activity } (U/\text{liter}) = \frac{\Delta r_T}{r_{ref}} \times \text{Lipase activity of reference standard } (U/\text{liter})$$

Alternatively, the lipase activity in the unknown sample may be calculated directly from the decrease in oxygen tension per minute after calibration of the system with primary linoleic acid standards (1 µmol of linoleic acid will consume 1 µmol of oxygen under the conditions of this assay). 1 (IUB) Unit results in the consumption of 1 µmol of $O_2$ per minute under the conditions of the assay.

While the subject invention has been described with relation to the preferred embodiments thereof, various modifications will now be apparent to one of ordinary skill in the art and is intended to cover all such modifications as fall within the scope of the appended claims.

I claim:

1. A method for the specific determination of lipase activity in a biological fluid comprising:
   (a) adding a sample of a biological fluid sample to an emulsified substrate, constituting a heterogeneous system, containing from about $1.0 \times 10^{-4}$ mole per liter to about $4.0 \times 10^{-4}$ mole per liter of a water-insoluble triglyceride having the structural formula:

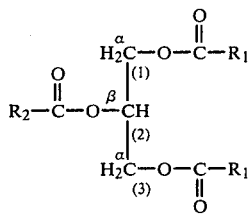

$R_1 =$

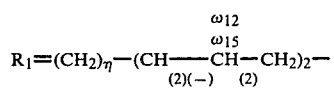

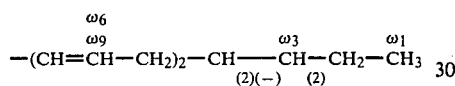

$n = 1, (2), 3, (4), 5$ $R_2 =$ a member selected from the group consisting of $R_1$ and saturated or (poly)unsaturated fatty acid alkyl chains;

and wherein said substrate also contains a bile salt;
   (b) simultaneously, or immediately thereafter, adding an amount of lipoxygenase high enough to convert the acid produced by lipolysis to its acid hydroperoxide at a rate sufficient to ensure that lipolysis is the limiting reaction but low enough to ensure that the rate of reaction with said substrate itself remains low; and
   (c) measuring the production of said acid hydroperoxide.

2. The method of claim 1 wherein trilinolein is employed as said substrate.

3. The method of claim 1 wherein said method is carried out at a pH of about 8.8 and at a temperature of about 30° C.

4. The method of claim 3 wherein the activity of said lipoxygenase is at least about 1,000 S.U./liter of substrate.

5. The method of claim 4 wherein the activity of said lipoxygenase is about 1,400 S.U./liter of substrate.

6. The method of claim 1 wherein lipase activity is determined by measuring spectrophotometrically the amount of linoleic acid hydroperoxide produced in a fixed incubation period.

7. The method of claim 6 wherein said fixed incubation period is effected by stopping the lipolytic reaction by adding an acid/alcohol mixture.

8. The method of claim 6 wherein said fixed incubation period is from about 5 to about 15 minutes.

9. The method of claim 6 wherein said spectrophotometric method is colorimetry.

10. The method of claim 9 wherein said colorimetric method is based on the capability of linoleic acid hydroperoxide to oxidize ferrous ion to ferric ion.

11. The method of claim 6 wherein said spectrophotometric method is UV spectrophotometry.

12. The method of claim 1 wherein said measurement of production of linoleic acid hydroperoxide is performed kinetically by measuring the rate of oxygen consumption.

13. An analytical procedure for the determination of lipase activity comprising adding an unknown sample fluid to a substrate reagent comprising an emulsion of trilinolein in a an amount of about $1.0 \times 10^{-4}$ to 4.0 to $10^{-4}$ mole per liter, adding an amount of lipoxygenase sufficient to insure that lipolysis is the rate limiting reaction and thereafter calculating lipase activity on the basis of production of linoleic acid hydroperoxide.

14. The method of claim 13 wherein said method is carried out at a pH of about 8.8 and at a temperature of about 30° C.

15. The method of claim 14 wherein the activity of said lipoxygenase is at least about 1,000 S.U./liter of substrate.

16. The method of claim 13 wherein the production of linoleic acid hydroperoxide is determined by spectrophotometry.

17. The method of claim 13 wherein the production of linoleic acid hydroperoxide is measured kinetically by monitoring the accompanying decrease in oxygen tension.

18. In a test for lipase activity wherein a triglyceride substrate in emulsified form is contacted with a test sample and lipase activity is measured as a function of the product formed by lipolysis, the improvement comprising:
   employing a substrate in a an amount of about $1.0 \times 10^{-4}$ to 4.0 to $10^{-4}$ mole per liter having the general formula;

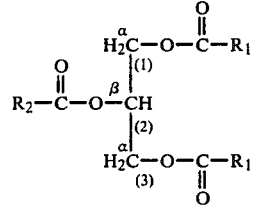

$R_1 =$

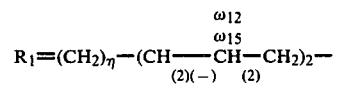

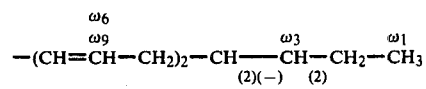

$\eta = 1, (2), 3, (4), 5$ $R_2 =$ a member selected from the group consisting of $R_1$ and saturated or (poly)unsaturated fatty acid alkyl chains;

and further employing a sufficient amount of lipoxygenase to ensure that the conversion of substrate to linoleic acid by lipolysis is the rate limiting reaction, and thereafter determining lipase activity as a function of the linoleic hydroperoxide produced.

19. The test of claim 18 wherein said substrate is trilinolein.

20. The test of claim 18 wherein said test sample, substrate and lipoxygenase are allowed to react at about 30° C. and at a pH of about 8.8.

21. The test of claim 18 wherein the activity of said lipoxygenase is at least about 1,000 S.U./liter.

* * * * *